United States Patent
Nakao et al.

[11] 3,993,780
[45] Nov. 23, 1976

[54] PHENOXYETHYLAMINE DERIVATIVES HAVING CENTRAL NERVOUS SYSTEM DEPRESSANT AND ANTI-HYPERTENSIVE ACTIVITY

[75] Inventors: Masaru Nakao; Kikuo Sasajima, both of Toyonaka; Isamu Maruyama, Minoo; Shigenari Katayama, Takarazuka; Hisao Yamamoto, Nishinomiya, all of Japan

[73] Assignee: Sumitomo Chemical Company, Limited, Japan

[22] Filed: Oct. 18, 1974

[21] Appl. No.: 515,889

[30] Foreign Application Priority Data
Oct. 25, 1973 Japan.............................. 48-120516.

[52] U.S. Cl............................ 424/330; 260/570.6; 260/570.7
[51] Int. Cl.²................................... A61K 31/135
[58] Field of Search.................... 424/330; 260/570.7

[56] References Cited
UNITED STATES PATENTS

| | | | |
|---|---|---|---|
| 3,171,858 | 3/1965 | L'Italien........................... | 260/570.5 |
| 3,225,096 | 12/1965 | Mills et al......................... | 260/570.5 |
| 3,457,270 | 7/1969 | Fleming et al..................... | 260/295 |
| 3,857,891 | 12/1974 | Holmes............................. | 260/570.7 |

*Primary Examiner*—Leonard Schenkman
*Attorney, Agent, or Firm*—Stewart and Kolasch, Ltd.

[57] ABSTRACT
Novel phenoxyethylamine derivatives of the formula:

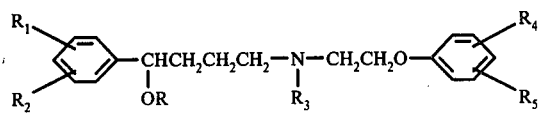

wherein $R_1$ and $R_2$ are each hydrogen, halogen, $C_1$–$C_4$ alkyl or $C_1$–$C_4$ alkoxy, $R_3$ is hydrogen or $C_1$–$C_4$ alkyl, $R_4$ and $R_5$ are each hydrogen or $C_1$–$C_4$ alkoxy and R is alkyl or aralkyl, and non-toxic pharmaceutically acceptable salts thereof, which are useful as central nervous system depressants and anti-hypertensive agents and can be prepared by reducing a compound of the formula:

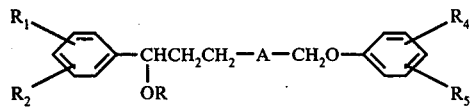

wherein $R_1$, $R_2$, $R_4$, $R_5$ and R are each as defined above and A is

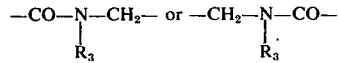

(wherein $R_3$ is as defined above) with a reducing agent.

23 Claims, No Drawings

PHENOXYETHYLAMINE DERIVATIVES HAVING CENTRAL NERVOUS SYSTEM DEPRESSANT AND ANTI-HYPERTENSIVE ACTIVITY

The present invention relates to novel phenoxyethylamine derivatives having central nervous system depressant activity and anti-hypertensive activity, and their preparation and use.

More particularly, it relates to novel phenoxyethylamine derivatives of the formula:

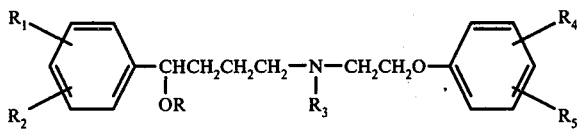

(I)

wherein $R_1$ and $R_2$ are each hydrogen, halogen, $C_1-C_4$ alkyl or $C_1-C_4$ alkoxy, $R_3$ is hydrogen or $C_1-C_4$ alkyl, $R_4$ and $R_5$ are each hydrogen or $C_1-C_4$ alkoxy and R is alkyl or aralkyl, and non-toxic pharmaceutically acceptable acid addition salts or N-acylated derivatives thereof, to a process for producing them and to pharmaceutical compositions comprising a phenoxyethylamine derivative of the formula (I) or its non-toxic pharmaceutically acceptable acid addition salt or N-acylated derivative with pharmaceutically acceptable carriers.

As used herein, the term "halogen" means chlorine, fluorine or bromine, preferably chlorine or fluorine. The term "$C_1-C_4$ alkyl" means straight or branched alkyl having one to four carbon atoms (e.g. methyl, ethyl, isopropyl, butyl, etc.). The term "$C_1-C_4$ alkoxy" means alkoxy having one to four carbon atoms (e.g. methoxy, ethoxy, isopropoxy, etc.). The term "alkyl" means alkyl having one to 10 carbon atoms, preferably one to four carbon atoms. The term "aralkyl" means benzyl, phenethyl or benzyl substituted by halogen, lower alkyl or lower alkoxy on the benzene ring. The term "N-acylated derivative" means N-formyl, N-acetyl, N-propionyl or N-benzoyl compounds of the phenoxyethylamine derivatives of the formula (I), preferably N-acetyl derivatives of the compound of the formula (I).

It has been found that the novel phenoxyethylamine derivatives of the formula (I) defined above have a central nervous system depressant activity and are useful as tranquilizers and anti-psychotic agents. They also have a hypotensive activity and are useful as anti-hypertensive agents.

Among the phenoxyethylamine derivatives of the formula (I), the compounds of the following formula are preferred:

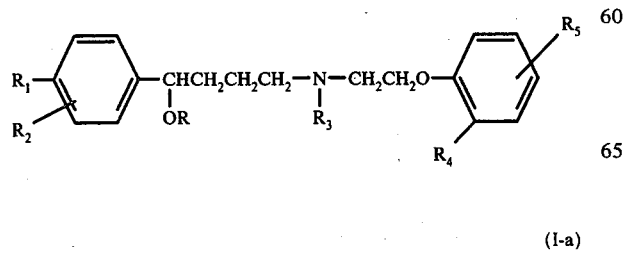

(I-a)

wherein $R_1$, $R_2$, $R_3$, $R_4$, $R_5$ and R are the same as defined in the formula (I), and more preferred compounds are the compounds of the formula (I-a) wherein $R_1$ is fluorine, chlorine or $C_1-C_4$ alkoxy, $R_2$ is hydrogen or $C_1-C_4$ alkoxy, $R_3$ is hydrogen, $R_4$ is $C_1-C_4$ alkoxy, $R_5$ is hydrogen or $C_1-C_4$ alkoxy and R is $C_1-C_4$ alkyl or benzyl.

A still more preferred class of the compounds of the formula (I-a) are those wherein $R_1$ is fluorine, methoxy, ethoxy or methyl, $R_2$ is methoxy or hydrogen, $R_3$ is hydrogen, $R_4$ is $C_1-C_4$ alkoxy, $R_5$ is hydrogen or methoxy and R is $C_1-C_4$ alkyl.

A further more preferred class of compounds may be represented by the formula:

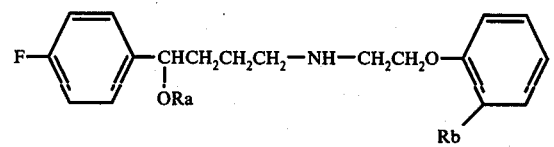

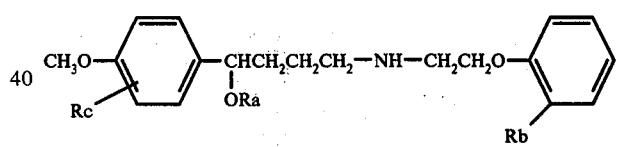

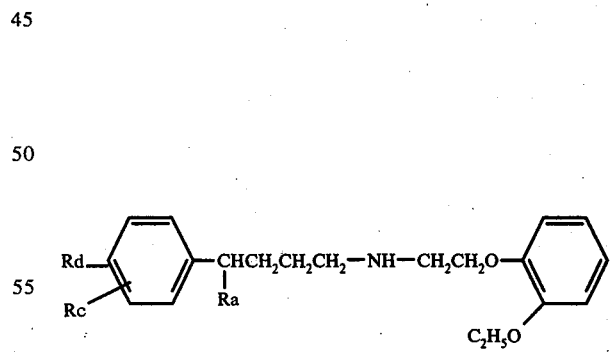

wherein Ra is $C_1-C_4$ alkyl, Rb is $C_1-C_4$ alkoxy, Rc is hydrogen or methoxy, and Rd is fluorine or methoxy.

Accordingly, a basic object of the present invention is to provide phenoxyethylamine derivatives of the formula (I) and their non-toxic pharmaceutically acceptable salts, which are useful as tranquilizers, antipsychotic agents and anti-hypertensive agents. Another object of the invention is to provide a process for producing the phenoxyethylamine derivatives of the formula (I) and their non-toxic pharmaceutically acceptable salts. A further object of the invention is to provide pharmaceutical compositions comprising at least one of the phenoxyethylamine derivatives of the formula (I) and their non-toxic pharmaceutically acceptable salts with at least one of the pharmaceutically acceptable carriers. Further objects of the invention will be apparent from the foregoing and subsequent descriptions.

According to the present invention, phenoxyethylamine derivatives of the formula (I) can be prepared by reducing a compound of the formula:

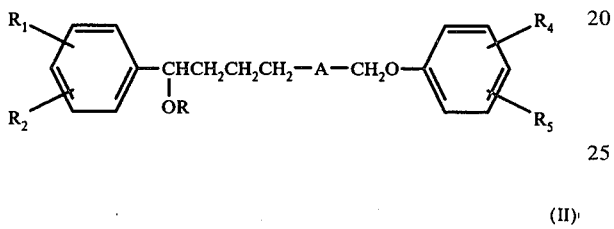

(II)

wherein $R_1$, $R_2$, $R_4$, $R_5$ and R are the same as defined above and A is a group of the formula:

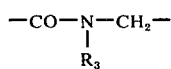

or

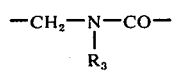

(wherein $R_3$ is as defined above) with a reducing agent.

The suitable reducing agents which can be preferably employed in the reaction are metal hydride complexes such as lithium aluminum hydride, diborane, sodium aluminum diethyl dihydride, sodium bis(2-methoxyethoxy)aluminum hydride, sodium borohydride with aluminum chloride, sodium borohydride with boron trifluoride, etc.

The reaction can be carried out in the presence of a suitable solvent which is inert under the reaction conditions. The preferred solvents are diethyl ether, diisopropyl ether, tetrahydrofuran, dioxane, methylal, N-ethylmorpholine, ethyleneglycol dimethyl ether, toluene and the like. The reaction can proceed at a temperature between about 0° C and 100° C using a stoichiometric amount or more of the said reducing agent. It is particularly preferred to carry out the reaction using lithium aluminum hydride in ether, tetrahydrofuran, toluene or a mixture thereof.

After the reaction is completed, the product can be isolated by the usual manner well known in the art and may be optionally further purified by any well known purification technique such as recrystallization.

The product can be isolated from the reaction system in the free base form or the acid addition salt form according to the procedures used and the product in the free form or the acid addition salt form can be converted to the other form using any conventional method in the art.

The phenoxyethylamine derivatives of the formula (I) can be converted to the corresponding N-acylated compounds by using a conventional N-acylating method, for example, by reacting them with an acylhalide, a carboxylic acid anhydride or a carboxylic acid ester.

The said N-acylated compounds may include the N-formyl, N-acetyl, N-propionyl and N-benzoyl derivatives of the compounds of the formula (I).

The phenoxyethylamine derivatives of the formula (I) also can be prepared by reacting a compound of the formula:

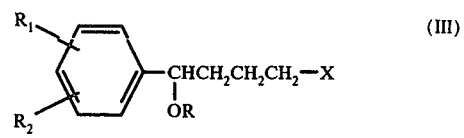

(III)

wherein $R_1$, $R_2$ and R are each as defined above and X is halogen or amino of the formula: $NHR_3$ (wherein $R_3$ is as defined above) with a compound of the formula:

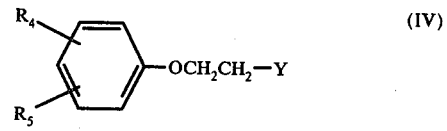

(IV)

wherein $R_4$ and $R_5$ are each as defined above and Y is amino of the formula: $NHR_3$ when X is halogen, or Y is halogen when X is amino of the formula: $NHR_3$, $R_3$ being as defined above.

The reaction may be carried out preferably in the presence of a suitable solvent, for example, benzene, toluene, xylene, acetone, methyl ethyl ketone, methyl isobutyl ketone, ethanol, isopropanol, sec.-butanol, tetrahydrofuran, dioxane, dimethylformamide, etc. The reaction can proceed at a temperature between about room temperature and the boiling point of the solvent used. The reaction is conducted preferably in the presence of a suitable acid-acceptor. Preferred acid-acceptors are sodium carbonate, sodium bicarbonate, sodium hydroxide, triethylamine, dimethylaniline, potassium acetate, etc. A small amount of potassium iodide or sodium iodide may be employed to accelerate the reaction. The reaction is usually completed within a period of 1 to 40 hours.

After the reaction is completed, the product can be isolated from the reaction system and purified using any conventional procedure in the art.

The thus obtained product can be converted to the corresponding N-acylated derivative in the same manner as mentioned above.

The compound of the formula (II) can be prepared by a conventional method, for example, by condensing a compound of the formula:

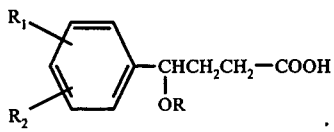

wherein $R_1$, $R_2$ and R are each as defined above or its reactive derivative (e.g. halide, anhydride, mixed anhydride) with a compound of the formula:

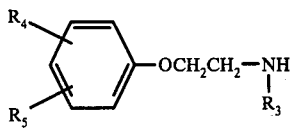

wherein $R_3$, $R_4$ and $R_5$ are each as defined above.

The compound of the formula (II) can also be prepared by condensing a compound of the formula:

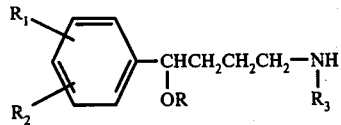

wherein $R_1$, $R_2$, $R_3$ and R are each as defined above with a compound of the formula:

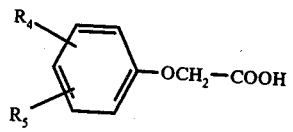

wherein $R_4$ and $R_5$ are as defined above or its reactive derivative (e.g. halide, anhydride, mixed anhydride).

The compound of the formula (II) can also be prepared by O-alkylating a compound of the formula:

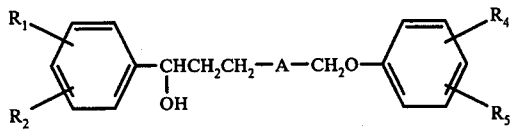

wherein $R_1$, $R_2$, $R_4$, $R_5$ and A are each as defined above using a conventional O-alkylating method.

The phenoxyethylamine derivatives of the formula (I) can be converted to the corresponding non-toxic pharmaceutically acceptable acid addition salts with suitable organic or inorganic acids by any conventional method.

The preferred acids are non-toxic pharmaceutically acceptable acids, for example, hydrochloric acid, sulfuric acid, phosphoric acid, hydrobromic acid, sulfamic acid, citric acid, oxalic acid, lactic acid, malic acid, fumaric acid, acetic acid, benzoic acid, mandelic acid, cinnamic acid, glycolic acid, tartaric acid, ascorbic acid and the like.

According to these processes, the following compounds, for example, can be obtained:

N-Ethyl-N-[4-ethoxy-4-(4-fluorophenyl)butyl]-2-(2-ethoxyphenoxy)ethylamine oxalate, M.P. 116° – 120° C;

N-[4-(4-Fluorophenyl)-4-methoxybutyl]-2-(2-ethoxyphenoxy)ethylamine oxalate, M.P. 104° – 107° C;

N-[4-(4-Fluorophenyl)-4-propoxybutyl]-2-(2-ethoxyphenoxy)ethylamine oxalate, M.P. 140° – 144° C;

N-[4-Butoxy-4-(4-fluorophenyl)butyl]-2-(2-ethoxyphenoxy)ethylamine oxalate, M.P. 129° – 131° C;

N-[4-(4-Fluorophenyl)-4-isopropoxybutyl]-2-(2-ethoxyphenoxy)ethylamine oxalate, M.P. 148°– 151° C;

N-[4-Benzyloxy-4-(4-fluorophenyl)butyl]-2-(2-ethoxyphenoxy)ethylamine oxalate, M.P. 117° – 120° C;

N-[4-Ethoxy-4-(4-fluorophenyl)butyl]-2-(2-methoxyphenoxy)ethylamine oxalate, M.P. 143° – 144° C;

N-[4-Ethoxy-4-(4-fluorophenyl)butyl]-2-(2-propoxyphenoxy)ethylamine oxalate, M.P. 133° – 136° C;

N-[4-Ethoxy-4-(4-fluorophenyl)butyl]-2-(2-isopropoxyphenoxy)ethylamine oxalate, M.P. 145° – 147° C;

N-[4-Ethoxy-4-(4-fluorophenyl)butyl]-2-(2-butoxyphenoxy)ethylamine oxalate, M.P. 126° – 130° C;

N-[4-(4-Chlorophenyl)-4-ethoxybutyl]-2-(2-ethoxyphenoxy)ethylamine oxalate, M.P. 125° – 128° C;

N-[4-Ethoxy-4-(4-methoxyphenyl)butyl]-2-(2-ethoxyphenoxy)ethylamine oxalate, M.P. 132° – 134° C;

N-[4-Ethoxy-4-(4-methylphenyl)butyl]-2-(2-ethoxyphenoxy)ethylamine oxalate, M.P. 148° – 151° C;

N-[4-(3,4-Dimethoxyphenyl)-4-ethoxybutyl]-2-(2-ethoxyphenoxy)ethylamine oxalate, M.P. 97° – 100° C;

N-[4-Ethoxy-4-(4-fluorophenyl)butyl]-2-(2,6-dimethoxyphenoxy)ethylamine oxalate, M.P. 121° – 124° C;

N-[4-(2,4-dimethoxyphenyl)-4-ethoxybutyl]-2-(2-ethoxyphenoxy)ethylamine oxalate, M.P. 92° – 96° C.

N-[4-Ethoxy-4-(4-fluorophenyl)butyl]-2-(2-ethoxyphenoxy)ethylamine oxalate, M.P. 157° – 160° C;

N-Acetyl-N-[4-ethoxy-4-(4-fluorophenyl)butyl]-2-(2-ethoxyphenoxy)ethylamine, M.P. 58° – 60° C.

The pharmacological evaluation of the compounds of the formula (I) has demonstrated that they possess a variety of depressant actions on the central nervous system. The compounds of the formula (I) are effective in the anti-apomorphine test and the test for the suppression of conditioned avoidance response in rats and also possess anti-methamphetamine and psychomotor depressant effects. For instance, N-[4-ethoxy-4-(4-fluorophenyl)butyl]-2-(2-ethoxyphenoxy)ethylamine oxalate has $ED_{50}$ of 1 mg/kg in anti-apomorphine activity, when tested according to P. A. J. Janssen et al's method ["Arzneimittel-Forschung", Vol. 15, No. 2, pages 104 – 117 (1965)]. Moreover, the compounds of the formula (I) have a potent hypotensive action and may be used as anti-hypertensive agents.

The phenoxyethylamine derivatives of the formula (I) and their non-toxic pharmaceutically acceptable salts can be administered orally or parenterally in an amount of 0.1 to 200 mg a day.

The compounds of the formula (I) and their non-toxic pharmaceutically acceptable salts thereof may be brought into a form suitable for administration according to a method known in the art.

They can be admixed with pharmaceutically acceptable carriers or diluents such as lactose, starch, magnesium stearate, magnesium carbonate, potassium phosphate, tragacanth, gelatin and sodium carboxymethylcellulose, and the resulting mixture or solution may be processed in usual manners to pharmaceutical dosage unit forms, for example, capsules, tablets, powder, pills, ampoules and the like.

The following examples are given to illustrate the invention more specifically but the invention is not in any way to be construed as being limited to these examples.

EXAMPLE 1

A solution of 3.0 g of N-[4-ethoxy-4-(4-fluorophenyl)butyryl]-2-(2-ethoxyphenoxy)ethylamine in 20 ml of tetrahydrofuran was added dropwise to a mixture of 0.6 g of lithium aluminum hydride and 40 ml of ether at 20° to 30° C while stirring, and the mixture was heated under reflux for 2 hours. After the reaction was completed, aqueous tetrahydrofuran was added dropwise to the reaction mixture slowly to decompose the unreacted, excessive reducing agent under cooling with ice. The precipitates were removed by filtration, and the filtrate was concentrated under reduced pressure. The resulting residue was extracted with benzene, washed with water, dried over anhydrous sodium sulfate and concentrated. The thus obtained oil was treated with oxalic acid and recrystallized from ethanol to give N-[4-ethoxy-4-(4-fluorophenyl)butyl]-2-(2-ethoxyphenoxy)ethylamine oxalate, M.P. 157° – 160° C. The above obtained crude oil was treated with acetic anhydride and crystallized from ether-hexane to give N-acetyl-N-[4-ethoxy-4-(4-fluorophenyl)butyl]-2-(2-ethoxyphenoxy)ethylamine, M.P. 58° – 60° C.

EXAMPLE 2

N-[4-Ethoxy-4-(4-fluorophenyl)butyl]-2-(2-ethoxyphenoxy)ethylamine oxalate was obtained in the same manner as described in Example 1 but replacing N-[4-ethoxy-4-(4-fluorophenyl)butyryl]-2-(2-ethoxyphenoxy)ethylamine by the same amount of N-[4-ethoxy-4-(4-fluorophenyl)butyl]-(2-ethoxyphenoxy)acetamide.

EXAMPLE 3

A mixture of 4.4 g of 4-ethoxy-4-(4-fluorophenyl)-butyl chloride, 3.6 g of 2-(2-ethoxyphenoxy)ethylamine, 2 g of sodium bicarbonate and 44 ml of N,N-dimethylformamide was stirred at about 110° C for 20 hours. After cooling, the reaction mixture was poured into cold water and extracted with benzene. The benzene layer was washed with water, dried over anhydrous sodium sulfate and concentrated under reduced pressure. The oily residue was treated with ethanolic oxalic acid and recrystallized from ethanol to give N-[4-ethoxy-4-(4-fluorophenyl)butyl]-2-(2-ethoxyphenoxy)-ethylamine oxalate, M.P. 157° – 160° C.

EXAMPLE 4

A mixture of 2 g of N-[4-ethoxy-4-(4-fluorophenyl)-butyl]amine, 2 g of 2-(2-ethoxyphenoxy)ethyl chloride, 0.1 g of sodium iodide, 1 g of sodium bicarbonate and 20 ml of N,N-dimethylformamide was stirred at about 110° C for 20 hours. After cooling, the reaction mixture was poured into 200 ml of water and extracted with benzene. The benzene layer was washed with water, dried over anhydrous sodium sulfate and concentrated under reduced pressure. The residue was treated with ethanolic oxalic acid and recrystallized from ethanol to give N-[4-ethoxy-4-(4-fluorophenyl)butyl]-2-(2-ethoxyphenoxy)ethylamine oxalate, M.P. 157° – 160° C.

What is claimed is:

1. A compound of the formula:

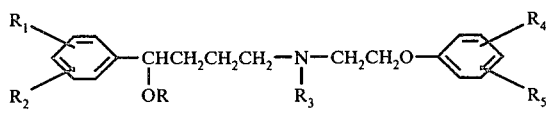

wherein $R_1$ and $R_2$ are each hydrogen, halogen, $C_1$–$C_4$ alkyl or $C_1$–$C_4$ alkoxy, $R_3$ is hydrogen or $C_1$–$C_4$ alkyl, $R_4$ and $R_5$ are each hydrogen or $C_1$–$C_4$ alkoxy and R is $C_1$–$C_{10}$ alkyl, benzyl, phenethyl or benzyl substituted by halogen, lower alkyl or lower alkoxy, non-toxic pharmaceutically acceptable acid addition salts thereof, or N-acylated derivatives thereof selected from the group consisting of N-formyl, N-acetyl, N-propionyl and N-benzoyl compounds thereof.

2. A compound of the formula:

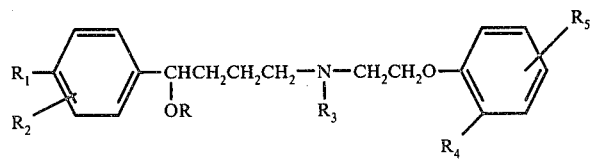

wherein $R_1$, $R_2$, $R_3$, $R_4$, $R_5$ and R are each as defined in claim 1, non-toxic pharmaceutically acceptable acid addition salts thereof, or N-acylated derivatives thereof as defined in claim 1.

3. A compound according to claim 2, wherein $R_1$ is fluorine, chlorine or $C_1$–$C_4$ alkoxy, $R_2$ is hydrogen or $C_1$–$C_4$ alkoxy, $R_3$ is hydrogen, $R_4$ is $C_1$–$C_4$ alkoxy, $R_5$ is hydrogen or $C_1$–$C_4$ alkoxy and R is $C_1$–$C_4$ alkyl or benzyl.

4. A compound according to claim 2, wherein $R_1$ is fluorine, methoxy, ethoxy or methyl, $R_2$ is methoxy or hydrogen, $R_3$ is hydrogen, $R_4$ is $C_1$–$C_4$ alkoxy, $R_5$ is hydrogen or methoxy and R is $C_1$–$C_4$ alkyl.

5. A compound of the formula:

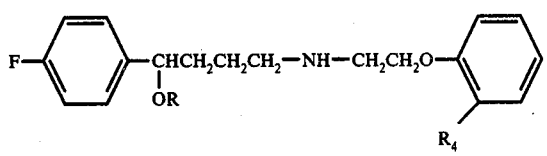

wherein R is C-C alkyl and $R_4$ is $C_1$-$C_4$ alkoxy, non-toxic pharmaceutically acceptable acid addition salts thereof, or the N-acetyl derivative thereof.

6. A compound of the formula:

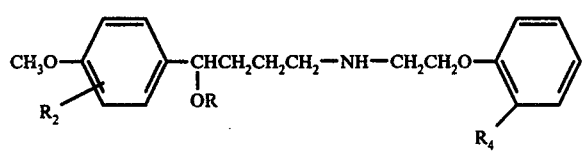

wherein R is $C_1$-$C_4$ alkyl, $R_2$ is hydrogen or methoxy and $R_4$ is $C_1$-$C_4$ alkoxy, non-toxic pharmaceutically acceptable acid addition salts thereof or the N-acetyl derivative thereof.

7. A compound of the formula:

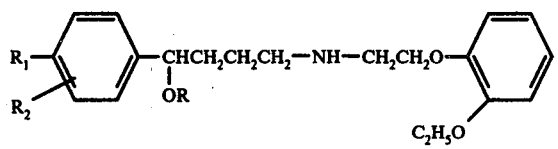

wherein $R_1$ is fluorine or methoxy, $R_2$ is hydrogen or methoxy and R is $C_1$-$C_4$ alkyl, non-toxic pharmaceutically acceptable acid addition salts thereof, or the N-acetyl derivative thereof.

8. N-[4-ethoxy-4-(4-fluorophenyl)butyl]-2-(2-ethoxyphenoxy)ethylamine.
9. N-[4-(4-fluorophenyl)-4-methoxybutyl]-2-(2-ethoxyphenoxy)ethylamine.
10. N-[4-(4-fluorophenyl)-4-n-propoxybutyl]-2-(2-ethoxyphenoxy)ethylamine.
11. N-[4-n-butyloxy-4-(4-fluorophenyl)butyl]-2-(2-ethoxyphenoxy)ethylamine.
12. N-[4-benzyloxy-4-(4-fluorophenyl)butyl]-2-(2-ethoxyphenoxy)ethylamine.
13. N-[4-ethoxy-4-(4-methoxyphenyl)butyl]-2-(2-ethoxyphenoxy)ethylamine.
14. N-[4-ethoxy-4-(4-methylphenyl)butyl]-2-(2-ethoxyphenoxy)ethylamine.
15. N-[4-ethoxy-4-(3,4-dimethoxyphenyl)butyl]-2-(2-ethoxyphenoxy)ethylamine.
16. N-[4-ethoxy-4-(2,4-dimethoxyphenyl)butyl]-2-(2-ethoxyphenoxy)ethylamine.
17. N-[4-ethoxy-4-(4-fluorophenyl)butyl]-2-(2-methoxyphenoxy)ethylamine.
18. N-[4-ethoxy-4-(4-fluorophenyl)butyl]-2-(2-isopropoxyphenoxy)ethylamine.
19. N-[4-ethoxy-4-(4-fluorophenyl)butyl]-2-(2-n-propoxyphenoxy)ethylamine.
20. N-[4-ethoxy-4-(4-fluorophenyl)butyl]-2-(2-butyloxyphenoxy)ethylamine.
21. N-[4-ethoxy-4-(4-fluorophenyl)butyl]-2-(2,6-dimethoxyphenoxy)ethylamine.
22. N-[4-ethoxy-4-(4-fluorophenyl)butyl]-2-(3,5-dimethoxyphenoxy)ethylamine.
23. A pharmaceutical composition useful as a tranquilizer, an anti-psychotic agent or an anti-hypertensive agent which comprises an effective tranquilizer, anti-psycotic or anti-hypertensive amount of the compound according to claim 1 and a pharmaceutically acceptable carrier or diluent.

* * * * *